United States Patent
Lin et al.

(10) Patent No.: US 7,569,105 B2
(45) Date of Patent: Aug. 4, 2009

(54) METHOD FOR MANUFACTURING DP-BIOGLASS COMPOSITION FOR USE IN DENTAL FRACTURE REPAIR

(75) Inventors: Feng Huei Lin, Taipei (TW); Chun-Pin Lin, Taipei (TW); Ching-Li Tseng, Taipei (TW)

(73) Assignee: National Taiwan University, Taipei (TW)

( * ) Notice: Subject to any disclaimer, the term of this patent is extended or adjusted under 35 U.S.C. 154(b) by 232 days.

(21) Appl. No.: 11/267,134

(22) Filed: Nov. 7, 2005

(65) Prior Publication Data

US 2006/0058172 A1 Mar. 16, 2006

(51) Int. Cl.
C03C 3/097 (2006.01)
C03C 3/078 (2006.01)
C03C 3/062 (2006.01)

(52) U.S. Cl. .............................. 106/35; 501/12; 501/63; 501/70; 501/73

(58) Field of Classification Search .................... 501/12, 501/63, 70, 73; 106/35
See application file for complete search history.

(56) References Cited

U.S. PATENT DOCUMENTS 4,994,414 A * 2/1991 Yamamoto et al. ............ 501/12
5,074,916 A * 12/1991 Hench et al. ................... 106/35

* cited by examiner

*Primary Examiner*—C. Melissa Koslow
(74) *Attorney, Agent, or Firm*—Rosenberg, Klein & Lee

(57) ABSTRACT

A method for manufacturing the DP-bioglass to use in dental fracture repair via the carbon dioxide laser, the method comprises the steps: mixing and co-dissolving silicon and phosphoric acid raw material into ethanol; sequentially adding nitric acid, calcium and sodium raw material and stirring; standing, drying, triturating and heating the composition to obtain a glass powder material consisting of $Na_2O$—$CaO$—$SiO_2$—$P_2O_5$ and drying the oxide material mixing with a phosphoric acid to react the DP-bioglass.

8 Claims, 1 Drawing Sheet

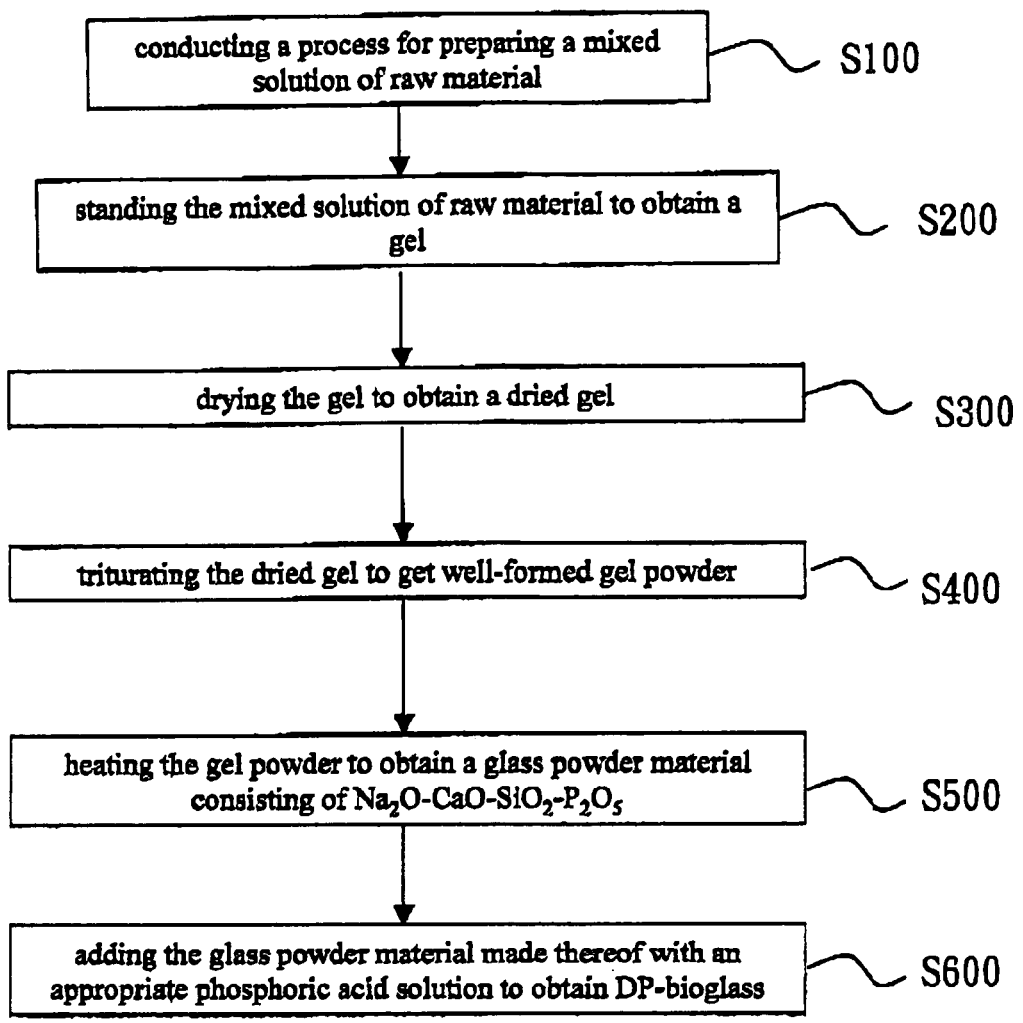

METHOD FOR MANUFACTURING DP-BIOGLASS COMPOSITION FOR USE IN DENTAL FRACTURE REPAIR

BACKGROUND OF THE INVENTION

1. Field of the Invention

The present invention relate to a method for manufacturing the dental fracture repair material. More specifically, the present invention discloses a method using the DP (Dicalcium Phosphate)-bioglass composition and carbon dioxide laser to repair the dental fracture.

2. Description of the Prior Art

The problems of clinical medicine are a plurality of cracks of tooth surface. When the crack extended to the pulp chamber, the disease passes through the crack into the pulp chamber to generate catabolism. According to the catabolism, the tissue fluid flowed out of the pulp chamber via the paths being the cracks. Therefore, the cracks of teeth did not have much effect on people in the beginning. When the cracks begun to expand and fracture, the teeth faces to extraction.

The teeth can have more or less cracks being attributed to the crystalline fault of the micro structure and the port of tooth falling. The defects have a bad effect on stress distribution of tooth, and the stress concentration on the parts accelerates the breakage. The breakage of object results from the inside defects or cracks, and it is important to prevent the teeth structure defects and the cracks generated.

So far, the dental fracture repair material used amalgam alloy or composite resin. Before the cracks or cavities are fixed, the cracks or cavities have to trim leading to expand the material touching area for the material adhering on the tooth. But, the trim not only damages the fracture area second times but also reduces the strength of teeth, even though the cavities completely fixed but the strength of tooth could not recover original. It is continued research in micro cracks of tooth for improving the strength of tooth.

In 1969, the Hench disclosed the bioglass including the $Na_2O$—$CaO$—$SiO_2$—$P_2O_5$ composition could bond to the bones. So far, the clinical application bioglass only used in alveolar ridge rebuilding and the tympanum fixed.

The wide research used laser irradiation in enamel and dentin but only the argon laser used to enhance polymerization of complex resin in dental fracture repair research In 1993, the Levy used the tricalcium phosphate mixing the 40 w.t. % phosphoric acid to be a dental fracture repair material filling into the cracks of tooth and irradiation of 10 W, Nd-YAG laser. After the laser irradiated on the material, the volume of material got bigger and filled in the cracks via absorbing heat generating the solid-liquid phase transfer to reduce the bacteria, passing through the cracks and dentinal tubule, infecting the pulp chamber, according to the SEM and polarizing research microscope. Further more, in 1977, the Bipin and Kenneth used the HF laser irradiated the amalgam alloy, complex resin and glass ionomer cement finding the mechanical fracture generated.

SUMMARY OF THE INVENTION

A primary object of the present invention is to provide a method for manufacturing DP-bioglass material for use in dental fracture repair. Said method uses DP-glass powder having a size less than 1 micron and a better homogeneity. In addition because said DP-bioglass requires lower temperature during heating, energy need during the manufacturing process is largely saved and the cost is therefore relatively low.

Another object of the present invention is to provide a method for manufacturing the DP (Dicalcium Phosphate)-bioglass composition to use in dental fracture repair via the carbon dioxide laser that uses the DP-bioglass mixing the phosphoric acid to be a dental fracture repair material and does not need expansive equipment to mass production.

A further object of the present invention is to provide a method for manufacturing the DP-bioglass composition to use in dental fracture repair via the carbon dioxide laser that uses the DP-bioglass composition and combines carbon dioxide laser to close the path of crack for preventing the micro cracks to expand.

Another object of the present invention is to provide DP-bioglass powder with lower cost and smaller size which can be mixed with phosphoric acid to form a DP-bioglass being able to prevent micro cracks from extending.

The vertical crack of teeth resulted in the accidental hurt including the scuff and particular occlusion. In this situation, a little crack is attributed to extend to the root and crown. When the crack extended to the pulp chamber, the disease passes through the crack into the pulp chamber to generate catabolism. According to the catabolism, the tissue fluid flowed out of the pulp chamber via the paths being the cracks. It is important to prevent the crack extend or even breakage.

The present invention comprises a DP-bioglass composition mixing the phosphoric acid to be a dental fracture repair material being similar to the glass ionomer cement, and uses the carbon dioxide laser to close the cracks. Further, the dental fracture repair material fills in the cracks of the tooth and reacts with the enamel and dentin to a calcium hydrogen phosphate ($CaHPO_4.2H_2O$). The crystalline phase between cracks and material is proof having the crosslink in room temperature, However, the calcium phosphate is not steady in mouth but it is transferred to calcium dihydrogen pyrophosphate ($CaP_2O_7$) by carbon dioxide laser.

So far, the breakage teeth in clinical therapy mostly extracted the teeth or fixed with complex resin, the teeth mostly lost the ability of chew after therapy. The present invention discloses a method using the DP-bioglass composition to fill in cracks and carbon dioxide laser to close the cracks. This process can completely prevent the micro crack to extend.

BRIEF DESCRIPTION OF THE DRAWINGS

The above and further objects, features and advantages of the invention will become clear from the following more detailed description when read with reference to the accompanying drawings in which:

The FIGURE shows a flow chart of the present invention,

DETAILED DESCRIPTION OF THE PREFERRED EMBODIMENTS

Before the micro cracks, carious teeth or cavities are fixed, the cracks, carious teeth or cavities have to trim but the trim not only damages the fracture area second times but also reduces the strength of teeth, even though the cavities completely fixed but the strength of tooth could not recover original. The present invention discloses using the laser to get the material and tooth to crosslink when the material fills in the cracks, and the teeth does not trim so that the material can steadily adhere on tooth for preventing the cracks to extend.

First, referring to FIG. 1, the present invention discloses a method for manufacturing the DP (Dicalcium Phosphate)-bioglass composition to use in dental fracture repair via the carbon dioxide laser, the method comprising the steps of:

Step 100, conducting a process for preparing a mixed solution of raw material, wherein the whole process needs to be stirred to get a good mixed solution of raw material. The overall stirring process takes 1 to 2 hours and the sequence of the addition of the raw material is as following: dissolving silicon-producing raw material like tetraethyl orthosilicate ($Si(OC_2H_5)_4$) and phosphoric acid-providing raw material like triethyl phosphate ester into ethanol($C_2H_5OH$); sequentially adding calcium-providing raw material like calcium nitrate tetrahydrate and sodium-providing raw material like sodium nitrate and mixing. In certain embodiments, this includes mixing and co-dissolving silicon and phosphoric acid raw material into ethanol; sequentially adding nitric acid, calcium and sodium raw material and stirring to form a mixed solution of raw material;

Step 200, standing the mixed solution of raw material under 60° C. for 7 to 10 days to obtain a gel;

Step 300, drying the gel under 220° C. for 20 hours to obtain a dried gel;

Step 400, triturating the dried gel to get well-formed gel powder;

Step 500, heating the gel powder under 800° C. for 4 hours to obtain a glass powder material whose ratio of $Na_2O$—$CaO$—$SiO_2$—$P_2O_5$ is 8.4 w.t. %, 40.6 w.t. % 39.0 w.t. % and 12 w.t. %; and Step 600, adding the glass powder material made thereof with an appropriate phosphoric acid solution to obtain DP-bioglass (dicalcium phosphate-bioglass powder), wherein the concentration of the phosphoric acid could be 65 w.t. % while the addition is 4-6 ml.

The DP-bioglass composition is a colloidal material to fill in the cracks of tooth using the carbon dioxide laser at 4 to 6 Watts, 0.6 to 0.8 mm beam, 4 to 6 seconds irradiation time, 50 to 60 seconds total irradiation time and the carbon dioxide laser with DP-bioglass interval is 0.5 to 1 mm.

The size of the DP-bioglass powder made by the present invention is about 50 micron and it is highly homogeneous. Besides, it can be triturated easily to obtain powder of size less than 1 micron. Furthermore, because the temperature of heating during the manufacturing of the glass powder is substantially lower than prior arts, energy need during the manufacturing process is largely reduced and the cost is efficiently saved.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of forming a DP-bioglass dental fracture repair composition via a carbon dioxide laser, the method comprising the steps:
    establishing a gel containing $Na_2O$—$CaO$—$SiO_2$—$P_2O_5$;
    drying the gel to obtain a dried gel;
    triturating the gel to form gel powder;
    heating the gel powder to obtain a DP-glass powder consisting of $Na_2O$—$CaO$—$SiO_2$—$P_2O_5$; and
    adding phosphoric acid to the DP-bioglass material to react the DP-bioglass.

2. The method according to claim 1, wherein the ratio of $Na_2O$—$CaO$—$SiO_2$—$P_2O_5$ of the DP-bioglass powder is 8.4 w.t. %, 40.6 w.t. %, 39.0 w.t. % and 12 w.t. %.

3. The method according to claim 1, wherein the standing procedure is under a condition of 60° C. for 7 to 10 days.

4. The method according to claim 1, wherein the drying procedure of the gel is under a condition of 220° C. for 20 hours.

5. The method according to claim 1, wherein the heating procedure of the gel powder is under a condition of 800° C. for 4 hours.

6. The method according to claim 1, wherein said phosphoric acid concentration is 65 w.t. % and adds 4 to 6 milliliters.

7. The method according to claim 1, wherein said DP-bioglass is a colloidal material.

8. A method of forming a DP-bioglass dental fracture repair composition via a carbon dioxide laser, the method comprising the steps:
    forming a mixed solution, the mixed solution including: silicon and phosphate raw materials mixed and co-dissolved into ethanol; and sequentially added nitric acid, calcium and sodium raw materials;
    wherein said sodium, calcium, silicon and phosphate raw materials are sodium nitrate ($NaNO_3$), calcium nitrate tetrahydrate ($Ca(NO_3)_2.4H_2O$), tetraethyl orthosilicate ($Si(OC_2H_5)_4$) and triethyl phosphate ester ($(OC_2H_5)_3PO$), respectively;
    standing the mixed solution of raw materials to obtain a gel;
    drying the gel to remove a liquid component and thereby obtain a dried gel;
    triturating the gel to form gel powder;
    heating the gel powder to obtain a DP-glass powder consisting of $Na_2O$—$CaO$—$SiO_2$—$P_2O_5$; and
    adding phosphoric acid to the DP-bioglass material to react the DP-bioglass.

* * * * *